US011969378B2

(12) United States Patent
Paulson

(10) Patent No.: US 11,969,378 B2
(45) Date of Patent: *Apr. 30, 2024

(54) SYSTEM FOR TREATMENT OF EYE CONDITIONS

(71) Applicant: Suzanne Paulson, Temecula, CA (US)

(72) Inventor: Suzanne Paulson, Temecula, CA (US)

(73) Assignee: EYEECO HOLDINGS, LLC, Blue Bell, PA (US)

( * ) Notice: Subject to any disclaimer, the term of this patent is extended or adjusted under 35 U.S.C. 154(b) by 1117 days.

This patent is subject to a terminal disclaimer.

(21) Appl. No.: 16/660,340

(22) Filed: Oct. 22, 2019

(65) Prior Publication Data

US 2020/0046549 A1    Feb. 13, 2020

Related U.S. Application Data

(63) Continuation-in-part of application No. 15/242,261, filed on Aug. 19, 2016, now Pat. No. 10,449,085.

(60) Provisional application No. 62/207,078, filed on Aug. 19, 2015.

(51) Int. Cl.
*A61F 7/02* (2006.01)
*A61F 7/00* (2006.01)
*A61F 9/04* (2006.01)

(52) U.S. Cl.
CPC .............. *A61F 7/02* (2013.01); *A61F 9/04* (2013.01); *A61F 2007/0004* (2013.01); *A61F 2007/0219* (2013.01); *A61F 2007/023* (2013.01); *A61F 2007/0242* (2013.01); *A61F 2007/0261* (2013.01)

(58) Field of Classification Search
None
See application file for complete search history.

(56) References Cited

U.S. PATENT DOCUMENTS

| 6,409,746 B1 * | 6/2002 | Igaki | A61F 7/03 607/114 |
|---|---|---|---|
| 6,641,264 B1 * | 11/2003 | Schwebel | A61F 9/029 351/158 |
| 7,231,922 B2 * | 6/2007 | Davison | A61F 9/029 351/158 |
| 2003/0056281 A1 * | 3/2003 | Hasegawa | A61N 2/002 2/206 |
| 2007/0049913 A1 * | 3/2007 | Grenon | A61H 7/00 607/104 |
| 2009/0287283 A1 * | 11/2009 | Biser | A61F 7/02 607/109 |
| 2011/0208279 A1 * | 8/2011 | Sanker | A61F 7/02 607/109 |
| 2012/0160240 A1 * | 6/2012 | Spano | A61F 9/04 128/202.19 |
| 2014/0330222 A1 * | 11/2014 | Bruder | A61F 13/124 604/290 |
| 2016/0120692 A1 * | 5/2016 | Chen | A61F 7/03 607/109 |

* cited by examiner

*Primary Examiner* — Joseph A Stoklosa
(74) *Attorney, Agent, or Firm* — BALLARD SPAHR LLP

(57) ABSTRACT

A dry eye treatment device is provided having a mask defining a treatment cavity which is positionable on a face of a user over the eyes. A temperature altering pack such as a gel pack is positionable within the treatment cavity and a fabric cover may surround the gel pack and have medication absorbed or placed upon the fabric material.

6 Claims, 3 Drawing Sheets

SYSTEM FOR TREATMENT OF EYE CONDITIONS

This application is a Continuation In Part of U.S. application Ser. No. 15/242,261, filed on Aug. 19, 2016, which claims priority to U.S. Provisional patent application Ser. No. 62/207,078, filed on Aug. 19, 2015, which is incorporated herein in its entirety by this reference thereto.

FIELD OF THE INVENTION

The system and method herein is generally related to the treatment of dry and irritated eye conditions. More particularly it relates to an eye treatment device configured for facial engagement to form a treatment cavity which controls the humidity to and around the eyes of the user. The disclosed device further provides a temperature component employable to communicate either heated or cooled temperatures to the eyes. Additionally, the disclosed device also provides for controlled application of medicine to the eyes and areas surrounding the eyes.

BACKGROUND OF THE INVENTION

Approximately 75% of the 60 million people suffering from dry eye experience a condition known as Evaporative Dry Eye. This results as a function of the tear quality of the patient which lacks sufficient oil therein. The remainder of dry eye sufferers are categorized as suffering from Aqueous Deficient Dry Eye. This results as a function of the quality and quantity of the tear production and communication of such to the eyes. People who suffer from such dry eye conditions often experience constant pain from eye irritation, including a sandy or gritty sensation. If left untreated, such dry eye conditions can lead to scarring or ulceration of the cornea, which can lead to a partial or total loss of vision.

Presently, there is no cure for dry eye conditions suffered by such patients. However, there exist various treatments that are designed to alleviate the often debilitating pain and discomfort caused by dry eye conditions. Such treatments include: artificial tear solutions, moisture chamber glasses, and punctal occlusion. While artificial tears primarily increase the comfort of people suffering from dry, irritated eyes, when used frequently, they may rinse away the natural tears necessary to reestablish a normal tear film. Frequent use of artificial tears is also expensive.

Another treatment includes the use of moisture chamber glasses. Moisture chamber glasses are custom-made products designed to alleviate the pain and discomfort caused by dry eye conditions. There are no commercially available moisture chamber glasses. They must be custom fit by an optician and can be prohibitively expensive for the average consumer. Further, because of the wide differential in the shape of the faces of patients, without a custom fitting of each patient for such chamber glasses, the comfort as well as seal of the chambers to the faces of users are marginal at best.

Thus, an unmet need exists for an apparatus, system and method for treating dry eye and/or irritated eye conditions which is comfortable to wear, adapted to fit well and seal with the facial structures of most patients, and which provides therapeutic benefits for the eyes without the discomfort, invasive nature, and limited use of the currently available treatments.

It should be noted, the forgoing examples of related art and limitations related therewith are intended to be illustrative and not exclusive, and they do not imply any limitations on the exercise device and method described and claimed herein. Various limitations of the related art are already known or will become apparent to those skilled in the art upon a reading and understanding of the specification below and the accompanying drawings

SUMMARY OF THE INVENTION

The present invention is directed towards a device and method for treating dry eyes and/or irritated eye conditions of a user. The device is configured for comfortable facial engagement to form a treatment cavity which controls and maintains humidity to the eyes of the user. Further, the device is employable to maintain and/or increase the temperature and humidity around the eyes to aid in limiting evaporation of natural and/or artificial tears.

In use, the device herein provides a means to employ a method for promoting healthy eyes during use, by aiding in thickening the lipid layer. The device may also be employed for controlled application of medicine to the eyes and the communication of heat or cold temperature to the eyes as needed.

In use, the system herein provides for the communication to the eyes of the user, of moist heat, which experimentation and studies have shown is more therapeutic than dry heat. Moist heat in experimentation has been shown to penetrate more deeply, promotes circulation, and hydrates the sensitive eye lid and surrounding skin.

The duration of communication of moist heat or cold to the area treated with the device herein, as well as the actual area of the face covered and treated, is significantly enhanced over the prior art devices and methods. Using the pliable flexible mask herein to form a single treatment chamber covering both eyes of the patient and the areas surrounding the eyes, the device is able to treat a much greater area of facial skin surrounding the eyes, while concurrently also treating the eyes and lid margin. The mask is formed of a flexible polymeric material and has a front wall transitioning to a sidewall portion, which is engaged to a sealing edge about the perimeter of the sidewall portion.

The mask is adapted for engagement using the biasing force of a strap to hold a sealing edge of the mask in sealed engagement to the face of a user in a significantly improved fashion. This improved seal, as well as comfort to the user, is provided through the inclusion of a strap pathway extending across the entire frontal surface of the mask, which experimentation has found to provide a much improved seal to the mask with the face. This is accomplished through the communication of a biased pushing of the entire pathway surface toward the face, while the strap concurrently pulls both ends of the mask toward the face through the engagement of the strap therewith.

A treatment chamber covering both eyes, the bridge of the nose and areas surrounding both eyes is formed by the sealed engagement of the sealing edge of the mask with the face of the user. The treatment chamber can incorporate a temperature altering pack or hot or cold packs, such as gel packs which may be pre-cooled or pre-heated before positioning within the treatment chamber. Other such temperature altering packs can be used such as using rice or buckwheat, or plastic beads, or other fill material in such a temperature altering pack, which will store a reservoir of heat or cold.

A woven or non-woven fabric cover is provided to engage upon the gel pack and may be employed to insulate the temperature differential from the eyes, to provide moisture to the cavity, and to also provide medication to the cavity and to the surface of the skin surrounding the eyes. By forming the covers from textile or other fabric which will absorb liquid or gel medications, such may be delivered into the treatment cavity. The covers are shaped complimentary to the shape of the gel pack, and may be employed with a pocket therein sized to engage the gel packs and may be formed of a variety of fabrics, texture and shapes.

The mask may utilize one large gel pack or two or more gel packs allowing for them to have the greatest performance. Preferably, a single gel pack having temperature-storing gel beads within the confines of a plastic envelope is employed. The plastic housing or envelope of the gel pack, can be creased in a center area to define a fold or hinge, to aid in both packaging of the gel packs in a reduced area, and to ensure the gel pack bends in a correct position, as it traverses the bridge of the nose to correctly position one half of the gel pack on each side of the nose.

The gel packs and fabric cover for the gel packs can easily be heated in a microwave, hot water, conventional oven, or cabi (used in spas to heat towels) using steam. Additionally, the gel packs can be cooled in ice, freezers, ice water, and refrigerators to provide cooling temperature communication to the eyes within the chamber. Further, the mask can be used with gel packs that are covered in fabric or without a cover.

It is an object of this invention to provide a device and system for treatment of dry eye conditions and irritated eyes that can be employed for immediate and long-lasting relief and will comfortably fit any patient when worn.

Still another object of this invention is to provide a device and method that aids in the application of particular medicines.

The invention, accordingly, comprises the features of construction, combination of elements, and arrangement of parts which will be exemplified by the constructions hereinafter set forth, and the scope of the invention will be indicated in the claims.

With respect to the above summary description, before explaining at least one preferred embodiment of the herein disclosed eye treatment system in detail, it is to be understood that the invention is not limited in its application to the details of construction and to the arrangement in the following description or illustrated in the drawings. The eye treatment system and method herein described, is capable of other embodiments and of being practiced and carried out in various ways which will become obvious to those skilled in the art on reading this disclosure. Also, it is to be understood that the phraseology and terminology employed herein are for the purpose of description and should not be regarded as limiting.

As such, those skilled in the art will appreciate that the conception upon which this disclosure is based, may readily be utilized as a basis for designing of other face-engageable eye treatment systems and devices and for carrying out the several purposes of the present disclosed system. It is important, therefore, that the claims herein be regarded, as including such equivalent construction and methodology, insofar as they do not depart from the spirit and scope of the present invention.

BRIEF DESCRIPTION OF DRAWING FIGURES

The accompanying drawings, which are incorporated herein and form a part of the specification, illustrate some, but not the only or exclusive examples of embodiments and/or features of the invention. It is intended that the embodiments and figures disclosed herein are to be considered illustrative rather than limiting.

DETAILED DESCRIPTION OF THE EXEMPLARY EMBODIMENTS

Figure 1:
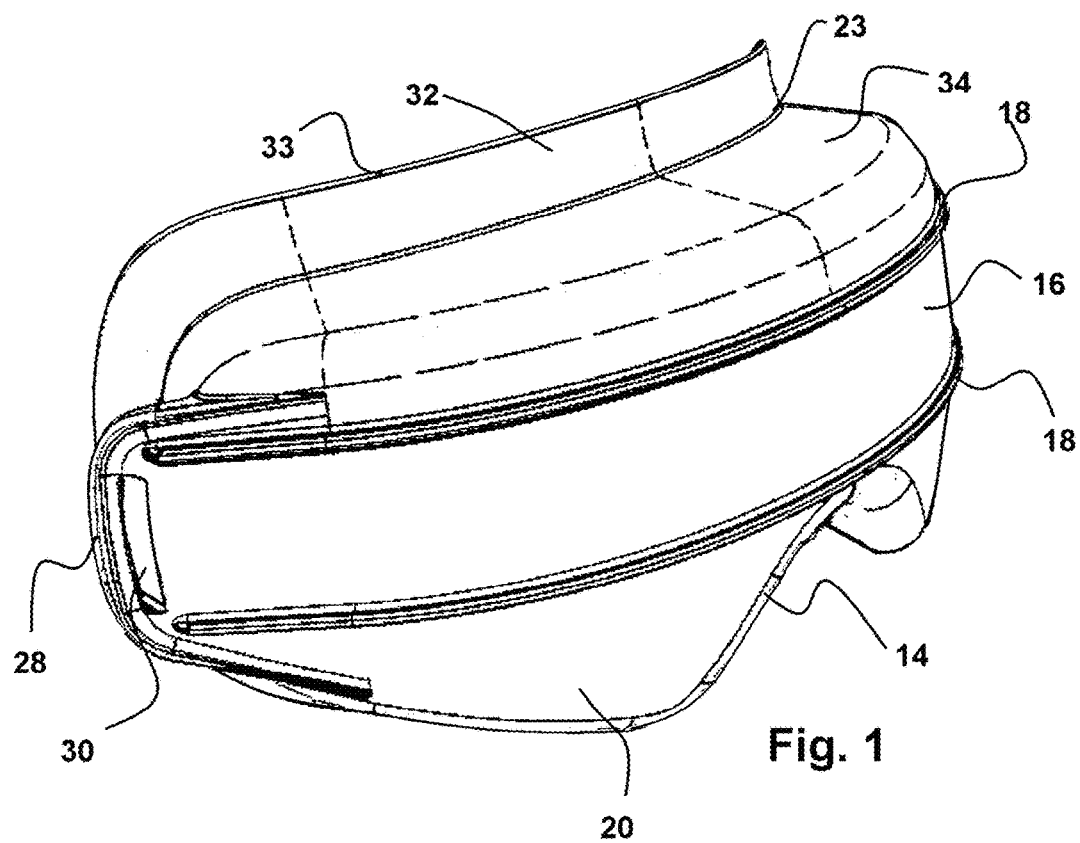
FIG. 1 is a front perspective view of the mask of the present invention showing the strap pathway communicating across the entire exterior front facing surface and showing a sealing edge adapted for sealed engagement with the face of a user thereby forming the treatment cavity.

In this description, any directional prepositions if employed, such as up, upwardly, down, downwardly, front, back, first, second, top, upper, bottom, lower, left, right and other such terms refer to the device or depictions as such may be oriented are describing such as it appears in the drawings and are used for convenience only. Such terms of direction and location are not intended to be limiting or to imply that the device herein has to be used or positioned in any particular orientation.

Now referring to drawings in FIGS. 1-5, wherein similar components are identified by like reference numerals, there is seen in FIG. 1 device 10 for treating dry eye and/or irritated eye conditions and which is configured to control, maintain and/or increase or decrease the temperature and humidity to and around the eyes of a user.

Figure 3:
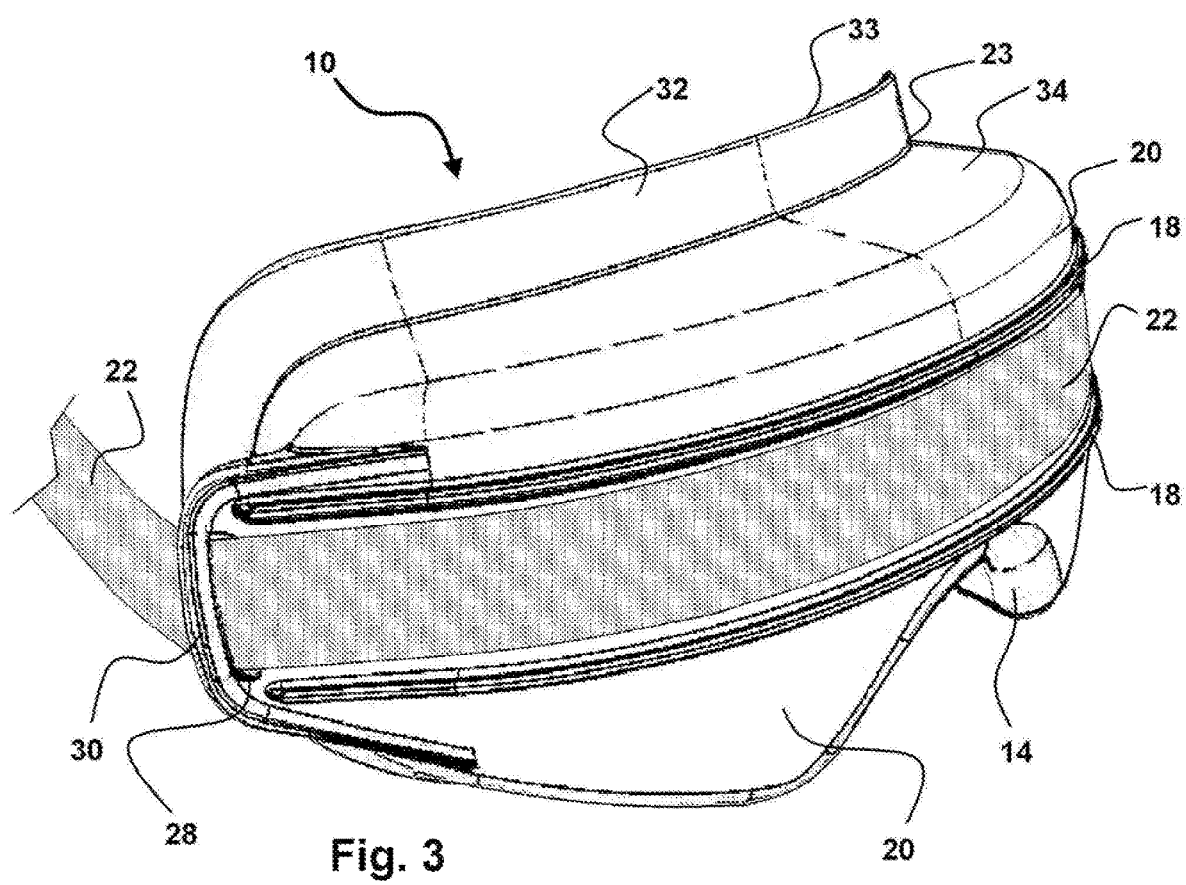
FIG. 3 is a view of the front wall of the mask as in FIG. 1, and also showing a strap communicating across the entire front wall surface through a formed strap pathway and communicating through strap apertures extending from an edge on both ends of the mask.

The device 10 shown in exploded view of the multiple components which may be used in FIG. 3, will concurrently communicate moisture to areas of the face and eyes positioned within a defined treatment cavity 12 of the mask 14 when positioned in an as-used position on the face of a patient or user. In such an as-used position, the mask is engaged over the eyes and facial areas surrounding the eyes and the treatment cavity 12 is defined an area within a sealed engagement to surround both eyes of the user and the skin surrounding and in-between their eyes.

Shown in FIG. 1 is a front perspective view of the mask 14 which is employed in all modes of the device 10 herein such as that in FIG. 3. Particularly preferred for the communication of even pressure to the mask 14, to hold it in sealed engagement to the face of a user, in the as used position, is the inclusion of a formed strap pathway 16 communicating across the entire front wall 20 of the mask 14 in-between opposing parallel ribs 18 extending away from the exterior surface of the front of the mask 14.

This formed pathway 16 when operatively engaged with a strap 22 as in FIG. 3, where the strap 22 contacts the entire front wall 20 along the pathway 16, provides an especially comfortable and enhanced sealed connection to the head of the user. This is because the strap 22, when tensioned around the back of the head of the user, and running across the entire pathway 16, provides a more even bias or forcing of the front wall 20, toward the face of the user, which communicates the even force and contact of the sealing edge 32 against the face of the user which is both more comfortable and less likely to leak during use.

Additionally, the pathway 16 directs the strap 22 at both ends of the mask 14, into and through apertures 28 formed in projections 30 extending from both ends of the mask 14. This engagement of the strap 22 is most preferred as it has been found that when the mask 14 is formed of a polymeric material, the combination of biasing force towards the face evenly across the pathway 16, yields sufficient force to hold the sealing edge 32 in sealed engagement with the face of the user. However, it has been found that it also yields a more comfortable engagement of the sealing edge 32 so the mask 14 may be comfortably worn for longer periods.

Of course the mask 14 can be employed with just a strap 22 engaged with the projections 30 by wrapping or engagement through the apertures 28, however this has been found not to yield the even pressure or bias toward the face of the user the positioning of the strap 22 across the entire pathway 16 yields.

Additionally, in the preferred mode of the strap 22 within the pathway 16, and engaged through the apertures 28 at both ends, in addition to providing a compression of the sealing edge 32 against the face with less pressure, also imparts a slight stretching or elongation of the body of the mask 14, at the two ends of the mask 14, in a pulling of the strap 22 at the ends to pull them in opposite directions. This slight stretching or elongation has been found to help maintain the mask 14 in the as-used position with the sealing edge 32 contacting the face of the user, as it tends to elongate or stretch the sealing edge 32 and remove wrinkles, and more evenly seal over the curve of the face.

So engaged, with the sealing edge 32 biased against the face, and stretched toward both ends by the engagement of the strap 22 through the apertures 28 in the projections 30, a treatment cavity 12 is formed. The treatment cavity 12 is defined by the area between the rear surface 21 of the front wall 20, the surface of the side wall 34 portion of the front wall, and the user's face, with the mask 14 in the as-used position.

Figure 2:
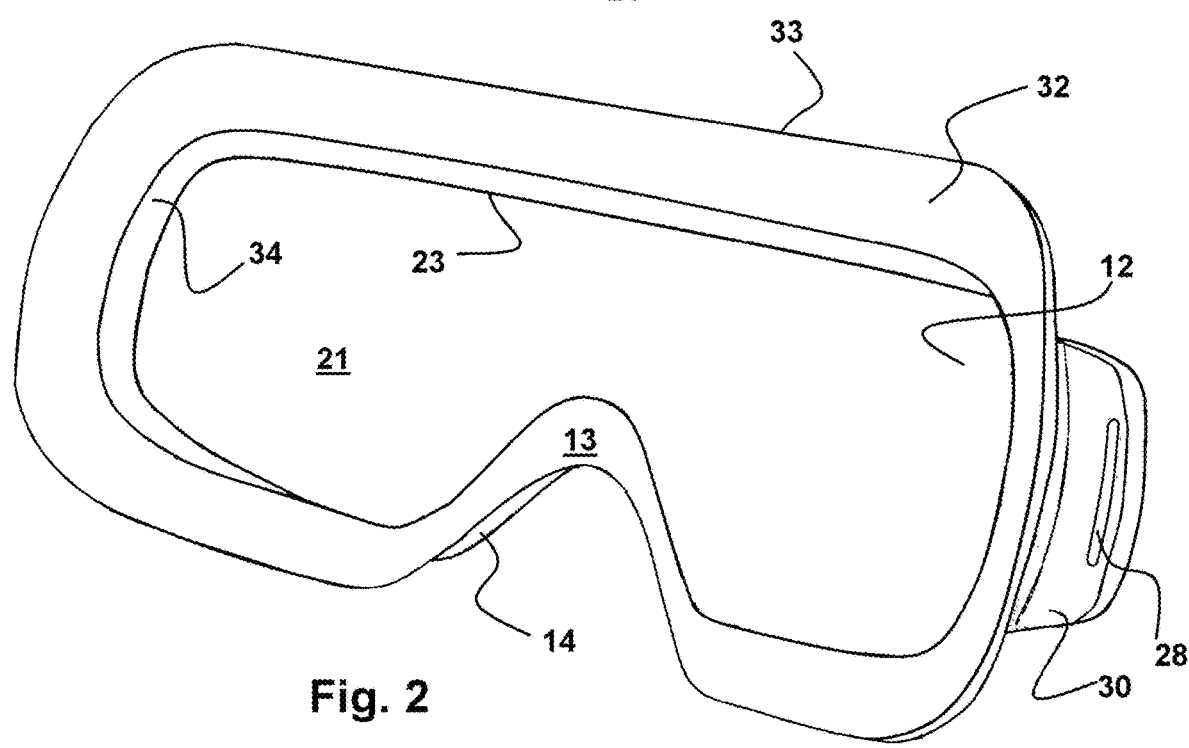
FIG. 2 is a rear perspective view of the mask of FIG. 1 for treating dry eye conditions and showing the treatment chamber defined by the front wall transitioning to form a sidewall communicating between the front wall and a sealing edge.

In FIG. 2, this treatment cavity 12, without the face of the user providing the rear wall, is shown. Also shown is the sealing edge 32 engaged at the perimeter edge 23 of the sidewall 34 portion of the front wall 20. This sidewall 34 defines a depth of the treatment cavity, and is a portion of the front wall 20 which transitions in curve or angle, from a direction running substantially parallel to the sealing edge 32, to the sidewall portion 34 which curves or angles to run a direction toward the sealing edge 32, and traverse to the direction thereof.

Further shown in FIG. 2, are one of the two projections 30 which position the two apertures 28 forming passages for the strap 22, at both ends of the mask 14. The projections 30 extend away from the mask 14 from both respective ends, to position the apertures 28 a distance beyond, the exterior perimeter edge 33 of the underlying sealing edge 32 of the mask 14. This positioning of the apertures 38 is preferred because as noted above, the strap 22 once tensioned around the head of the user, will bias the front wall 20 and the sidewall portion thereof, toward the face of the user. Concurrently the two ends of the mask 14 and portions of the sealing edge 32, are pulled in opposite directions, which as noted has been found to improve contact of the sealing edge 32 over the contours of the user's face, to help maintain the mask 14 in a sealed engagement to the face of the user. The force of the strap 22 being imparted across the entire pathway, along with the slight stretching of the sealing edge 32, increases user comfort by minimizing the force imparted to the mask 14 against the face to maintain the seal.

Figure 4:
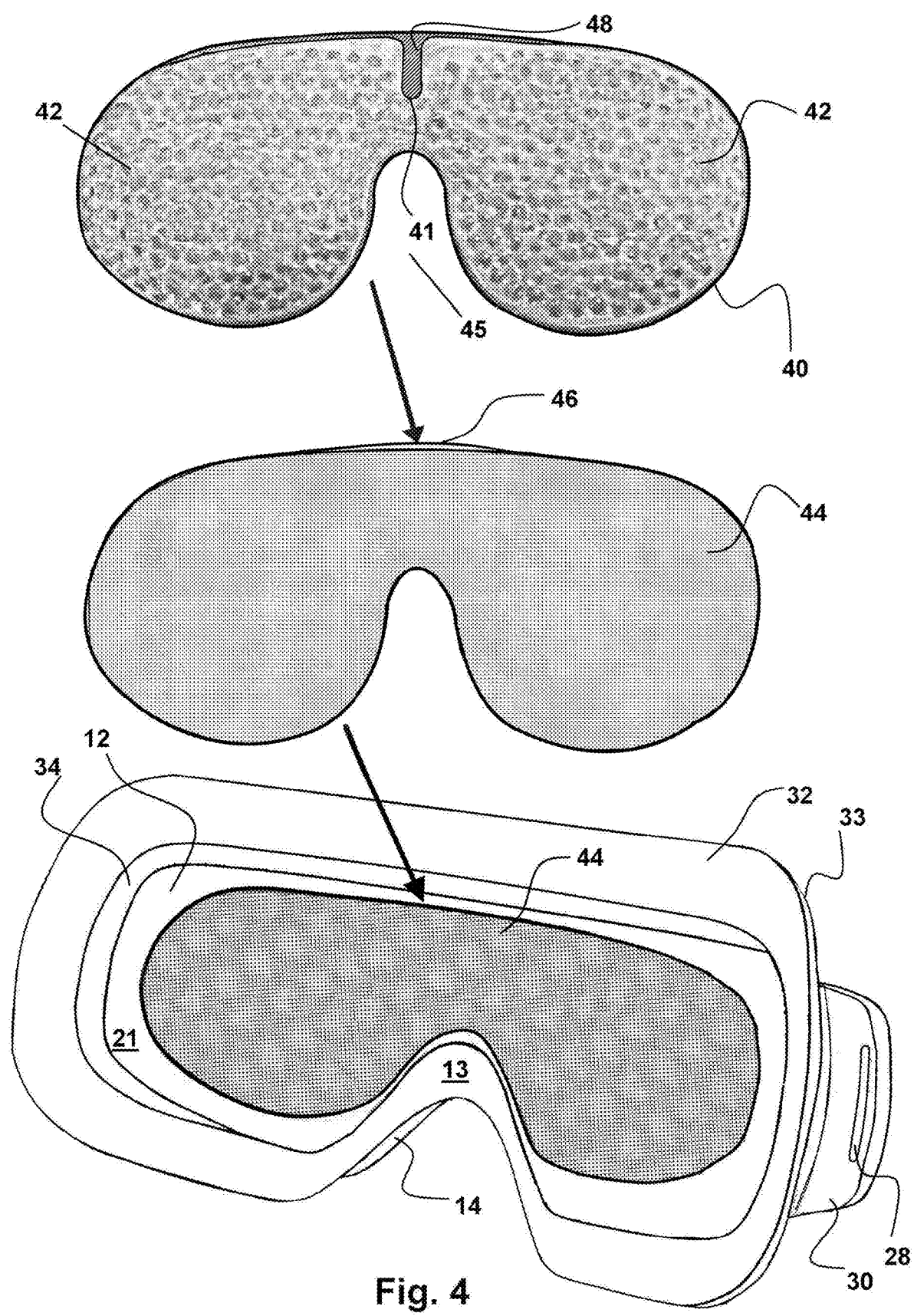
FIG. 4 shows an exploded view of a gel pack which is configured to engage within the treatment cavity of the mask, and which preferably is inserted into a fabric cover prior to operative placement in the treatment cavity.

Shown in FIG. 4 is an exploded view of all the components of the preferred mode of the device 10. As can be seen, a temperature altering pack, such as a gel pack 40, is depicted which has two rounded or circular lobes 42 separated by a recess 45 in one edge. The lobes 42 are sized to fit into the treatment cavity 12 and cover both eyes of the user, and the recess 45 is complimentary to the shape of the bridge 13 formed in the mask 14 which traverses over the nose of the user.

The gel pack 40 is filled with gel material which will store and provide a reservoir of transmittable heat or cold when engaged within the treatment cavity 12 with the mask 14 mounted to the as-used position. While defined as a gel pack 40 herein, any temperature altering pack or component, which may be heated or cooled, to generate heat or cold within the treatment cavity 12, is considered a gel pack 14. Also shown, is a preferred fabric cover 44 which has an opening 46 between the two sidewalls of the cover 44 for insertion of the gel pack 40 therein into an interior cavity. The gel pack 40 is preferably inserted within the fabric cover prior to engagement within the treatment cavity 12 and provides a more comfortable transmission of heat or cold than the plastic pouch defining the gel pack 40.

The cover 44 is preferably formed of a soft woven or non woven textile material such as cotton, bamboo, polynosic rayon, and other soft textile fabrics. The cover is formed in a shape, complimentary to the shape of the gel pack 40. The use of the fabric cover 44 is preferred as it increases the utility of the device 10 in that it which can be moistened and/or impregnated with medication or other treatments. Such treatment can be employed for one or both of the skin and the eyes when positioned within the treatment cavity 12 with the gel pack 40 inserted within.

Including the cover 44 thus allows for the inclusion of a wide variety of medical and/or cosmetic treatments along with moisture which may be communicated to and around the eyes of the user in differing treatments. Further the gel pack 40 may be heated or cooled prior to insertion into the cover 44 and the treatment cavity, to provided a symbiotic combination with the medication and/or moisture and/or heat to the cosmetic or medicinal treatment imparted to the cover 44 when positioned within the treatment cavity 12 of the mask 14.

Figure 5:
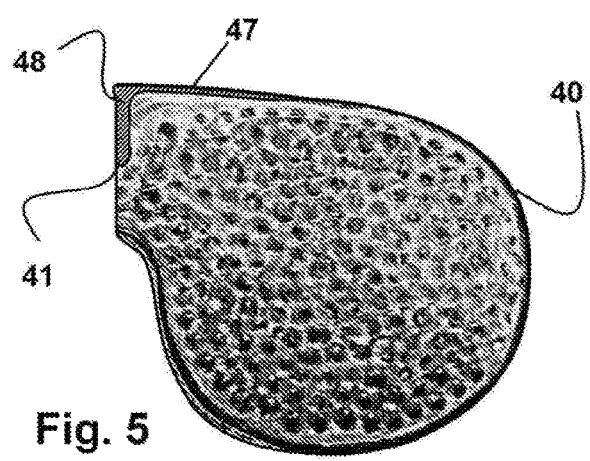
FIG. 5 depicts the gel pack in an evenly folded position which is enabled a formed hinge, whereby the gel pack bends on the hinge properly during use and is more evenly heated and more easily shipped.

Additionally shown in FIG. 4 and FIG. 5, is a hinge 48 or defined folding position at a central area of the gel pack 40 between the lobes 42. This hinge 48 is formed at a point in the plastic or polymeric material forming a flexible envelope 47 for the gel pack 40, by a fusing of a portion 41 of the two sidewalls defining the envelope 47 of the gel pack 40 at a central area. This fused portion 41 projects inward from the perimeter edge of the gel pack 40. This hinge 48 when so formed in a central area substantially centered between both ends and both lobes of the gel pack 40, is particularly preferred to provide a defined folding point, over the bridge of the nose of the user during use to operatively and equally position one of the two circular portions of the gel pack 40, properly over a respective eye of the user.

Further, the hinge 48 has also been found to help in both compacting shipment of the gel pack 40, by forming a centered fold without emptying all the contents of one circular area into the other circular area. Still further, when heating the gel pack 40 in a microwave oven, by positioning both of the two circular areas in substantial alignment, in a stack when folded such as shown in FIG. 5, a more even heating of both sides of the gel pack 40 occurs. The formed hinge 48 provides a means to form this fold of the gel pack 40 in the center every time, and thereby form the folded stack.

Although the invention has been described with respect to particular embodiments thereof, it should be realized that various changes and modifications may be made therein without departing from the spirit and scope of the invention. While the invention as shown in the drawings and described in detail herein discloses arrangements of elements of particular construction and configuration for illustrating preferred embodiments of structure and method of operation of the present invention, it is to be understood, however, that elements of different construction and configuration and other arrangements thereof, other than those illustrated and described, may be employed in accordance with the spirit of this invention. Any and all such changes, alternations and modifications as would occur to those skilled in the art are considered to be within the scope of this invention as broadly defined in the appended claims.

Further, the purpose of the attached abstract is to enable the U.S. Patent and Trademark Office and the public generally, especially scientists, engineers and practitioners in the art who are not familiar with patent or legal terms or phraseology to determine quickly, from a cursory inspection, the nature and essence of the technical disclosure of the application. The abstract is neither intended to define the invention of the application, which is measured by the claims, nor is it intended to be limiting as to the scope of the invention in any way.

What is claimed is:

1. A dry eye treatment apparatus, comprising:
   a mask, said mask having a front wall extending to a sealing edge which extends a length of said sealing edge from a first side of said sealing edge at a perimeter edge of said front wall, to a perimeter edge of said sealing edge;
   a strap pathway formed upon an exterior surface of said front wall, said strap pathway running between a first end of said mask to a second end of said mask;
   said strap pathway defining a path for a biased contact of a strap adapted for holding said mask upon a face of a user;
   a treatment cavity defined by an area between a rear surface of said front extending to said perimeter edge of said front wall;
   a temperature altering pack sized for positioning within said treatment cavity, for communicating heat or cold to said treatment cavity; and
   wherein said mask is positionable with said sealing edge surrounding the eyes of said user in a contact with a face of said user, thereby positioning said treatment cavity in front of the eyes of said user, in an as-used position of said mask.

2. The dry eye treatment apparatus of claim 1, additionally comprising:
   said strap pathway defined by an area between a pair of ribs extending away from said exterior surface of said front wall.

3. The dry eye treatment apparatus of claim 2, additionally comprising:
   a first projection extending from said first end of said mask to a distal end of said first projection;
   a first aperture formed in said first projection adjacent said distal end of said first projection;
   a second projection extending away from said second end of said mask, to a distal end of said second projection;
   a second aperture formed in said second projection adjacent said distal end of said projection.

4. The dry eye treatment apparatus of claim 2, additionally comprising:
   said temperature altering pack formed of a flexible envelope having material therein adapted for heating or cooling;
   said temperature altering pack having two lobes separated by a recess depending at a central area into one side edge which is complimentary in shape to a bridge of said mask.

5. The dry eye treatment apparatus of claim 1, additionally comprising:
   a first projection extending from said first end of said mask to a distal end of the first projection;
   a first aperture formed in said first projection adjacent said distal end of the first projection;
   a second projection extending away from said second end of said mask, to a distal end of the second projection;
   a second aperture formed in said second projection adjacent said distal end of the second projection.

6. The dry eye treatment apparatus of claim 1, additionally comprising:
   said temperature altering pack formed of a flexible envelope having material therein adapted for heating or cooling;
   said temperature altering pack having two lobes separated by a recess depending at a central area into one side edge which is complimentary in shape to a bridge of said mask.

* * * * *